US009629888B2

(12) United States Patent
Lo et al.

(10) Patent No.: US 9,629,888 B2
(45) Date of Patent: Apr. 25, 2017

(54) COMPOSITION OF MATTER FOR DELIVERING LIPID-SOLUBLE MATERIALS, AND A METHOD FOR PRODUCING IT

(75) Inventors: Yangming Martin Lo, Ashton, MD (US); Ansu Elizabeth Cherian, Washington, DC (US); Neil Allen Belson, Port Tobacco, MD (US)

(73) Assignees: LeafPro, LLC, Wilson, NC (US); University of Maryland, College Park, College Park, MD (US)

( * ) Notice: Subject to any disclaimer, the term of this patent is extended or adjusted under 35 U.S.C. 154(b) by 0 days.

(21) Appl. No.: 13/582,655

(22) PCT Filed: Mar. 7, 2011

(86) PCT No.: PCT/US2011/027399
§ 371 (c)(1),
(2), (4) Date: Nov. 15, 2012

(87) PCT Pub. No.: WO2011/109809
PCT Pub. Date: Sep. 9, 2011

(65) Prior Publication Data
US 2013/0059795 A1   Mar. 7, 2013

Related U.S. Application Data

(60) Provisional application No. 61/311,072, filed on Mar. 5, 2010.

(51) Int. Cl.
| | | |
|---|---|---|
| A61K 36/81 | (2006.01) | |
| A23L 33/185 | (2016.01) | |
| A23L 33/155 | (2016.01) | |
| A61K 9/14 | (2006.01) | |
| A61K 47/42 | (2006.01) | |
| A61K 47/46 | (2006.01) | |
| A61K 36/21 | (2006.01) | |
| A61K 36/47 | (2006.01) | |
| A61K 38/00 | (2006.01) | |

(52) U.S. Cl.
CPC ............ *A61K 36/81* (2013.01); *A23L 33/155* (2016.08); *A23L 33/185* (2016.08); *A61K 9/146* (2013.01); *A61K 9/148* (2013.01); *A61K 36/21* (2013.01); *A61K 36/47* (2013.01); *A61K 47/42* (2013.01); *A61K 47/46* (2013.01); *A23V 2002/00* (2013.01); *A61K 38/00* (2013.01)

(58) Field of Classification Search
CPC ........ A61K 36/81; A61K 9/146; A61K 9/148; A61K 36/21; A61K 36/47; A61K 47/42; A61K 47/46; A61K 38/00; A23L 33/185; A23L 33/155; A23V 2002/00
See application file for complete search history.

(56) References Cited

U.S. PATENT DOCUMENTS

| | | | | |
|---|---|---|---|---|
| 3,787,591 | A | * | 1/1974 | Hagiwara ................ A23G 3/48 424/750 |
| 4,144,895 | A | | 3/1979 | Fiore |
| 4,554,337 | A | | 11/1985 | Krinski |
| 4,737,367 | A | | 4/1988 | Langer |
| 5,462,593 | A | | 10/1995 | Poppe |
| 5,597,595 | A | | 1/1997 | DeWille |
| 6,290,974 | B1 | | 9/2001 | Swaisgood |
| 2002/0182250 | A1 | | 12/2002 | Hori |
| 2002/0197688 | A1 | * | 12/2002 | Pandolfino .................... 435/161 |
| 2004/0161435 | A1 | * | 8/2004 | Gupta ........................... 424/401 |
| 2005/0142114 | A1 | * | 6/2005 | Gieseler et al. ............. 424/93.2 |
| 2005/0147572 | A1 | * | 7/2005 | Giacomoni et al. ............ 424/59 |
| 2007/0264222 | A1 | * | 11/2007 | Georgiades ..................... 424/74 |
| 2008/0254514 | A1 | * | 10/2008 | Knudsen ...................... 435/71.1 |
| 2010/0093054 | A1 | | 4/2010 | Lo |
| 2011/0053224 | A1 | | 3/2011 | Lo |

FOREIGN PATENT DOCUMENTS

| | | | |
|---|---|---|---|
| CN | 1137870 | * | 12/1996 |
| CN | 101450088 | * | 6/2009 |
| CN | 101450152 | * | 6/2009 |

(Continued)

OTHER PUBLICATIONS

Hudson and Karis, Stability of Lipids and Proteins in Leaf Protein Concentrates, J. Sci. Fd Agric., 1976, 27, 443-448.*
Siebrits et al., The relative nutritive value of lucerne leaf protein concentrate (LPC) coagulated by means of steam or hot water, S.-Afr. Tydskr. Veek., 1986, 16(3) pp. 143-145.*
Ansu E. Cherian, Feasibility of Soluble Leaf Proteins as a Carrier for Vitamin D, Masters Thesis, Univ. of Maryland, 2009.*
Abismail, B, J. Canseiler, A. Wilhelm, H. Delmas and C.Gourdon (1999), "Emulsification by ultrasound: drop size distribution and stability." Ultrasonics Sonochemistry 6:75-83.

(Continued)

*Primary Examiner* — Lianko Garyu
*Assistant Examiner* — Joseph Fischer
(74) *Attorney, Agent, or Firm* — Nash & Titus, LLC

(57) ABSTRACT

This invention describes a novel composition of matter describing a complex comprising leaf protein and a lipophilic substance(s), along with the method of producing it. Delivery of lipid-soluble materials into the body is challenging because they are generally highly insoluble in water and very subject to oxidative degradation. The inventors have found that leaf protein—the water-soluble proteins derived from plant leaves—can efficiently form a complex with lipophilic materials. This leaf protein—lipid-soluble material complex is an effective carrier of lipophilic substances. As such, the leaf protein—lipid-soluble material complex disclosed herein can be used for the delivery of lipophilic vitamins, fatty acids, caretenoids, lipophilic drugs, and other lipophilic materials. This complex can be used to deliver lipophiles in foods, nutritional and dietary supplements, topical compositions and in pharmaceutical products.

8 Claims, 5 Drawing Sheets

(56) References Cited

FOREIGN PATENT DOCUMENTS

| GB | 867190 | * | 10/1957 | |
|---|---|---|---|---|
| WO | WO 2007/083316 | | 7/2007 | |
| WO | WO2008/143914 | * | 11/2008 | ............... C07K 1/14 |
| WO | WO 2008/143914 | | 11/2008 | |
| WO | WO2008143914 A1 | * | 11/2008 | |
| WO | WO 2010/045648 | | 4/2010 | |
| WO | WO2010045648 A1 | * | 4/2010 | |

OTHER PUBLICATIONS

Allison S., A. Dong A, J. Carpenter (1996), "Counteracting effects of thiocyanate . . . ", Biophysical Journal 71: 2022-2032.
Banville, C, J. Villemard, C. Lacroix (2000), "Comparison of different methods for fortifying Cheddar cheese with Vitamin D." International Dairy Journal 10: 375-382.
Carrasquilo KG, Sanchez C, Griebenow K (2000), "Relationship between conformational stability and lyophilisation . . . " Biotechnology and Applied Biochemistry, 31, 41-53.
Forrest, S., R. Yada, D. Rousseau (2005), "Interactions of vitamin D3 with bovine f3-lactoglobulin A and -casein." J. of Agricultural and Food Chemistry 53:8003-09.
Fu, H., P. Machado, T. Hahm, R. Kratochvil, C. Wei and Y. Lo (2010), "Recovery of nicotine-free proteins . . . " Bioresource Technol: 101 (6): 2034-2042.
Hudson, B and I. Karis (1973), "Aspects of vegetable structural lipids.I. The lipids of leaf protein concentrate." Journal of the Science of Food and Agriculture 24: 1541-1550.
Hsu, C. H. Nguyen, D. Yeung, D. Brooks, G. Koe, T. Bewley, R. Pearlman (1995), "Surface denaturation at solid-void interface—. . . " Pharm. Res. 12: 69-77.
Mozafari, M, C. Johnson, S. Hatziantoniou, C. Demetzos (2008), "Nanoliposomes and their applications in food nanotechnology." Journal of Liposome Research 18: 309-327.
Qi, M., N. Hettiarachchy, U. Kalapathy (1997), "Solubility and emulsifying properties of soy protein isolates modified by pancreatin." J. Food Sci. 62(6): 1110-1115.

Semo E, Kesselman E, Danino D, Livney D (2007), "Casein micelles as a natural nano-capsular vehicle for nutraceuticals." Food hydrocolloids, 21, 936-942.
Sharma A, U. Sharma (1997), "Liposomes in drug delivery: progress and limitations." International Journal of Pharmaceutics 154: 123-140.
Sheen J., (1991), "Comparison of chemical and functional properties of soluble leaf proteins from four plant species." Journal of Agricultural and Food Chemistry, 39, 681-685.
Sheen, J. V. Sheen (1985), "Functional properties of Fraction 1Protein from tobacco leaf." Journal of Agricultural and Food Chemistry 33: 79-83.
Tso, T. C. (2006), "Tobacco research and its relevance to science, medicine and industry." Contributions to Tobacco Research 22: 133-146.
Tso, T. C. (1990). Production, Physiology, and Biochemistry of Tobacco Plant, Ch. 22: Organic Metabolism—Tobacco Proteins. Ideals Inc., Beltsville, MD.
Tso, T. S. Kung (1983) "Soluble proteins in tobacco . . . " In: Leaf Protein Concentrates, Tehel L and Graham DG (eds.), Avi Publishing Company Inc., Connecticut, pp. 117-131.
Wang, Q., J. Allen and H. Swaisgood (1997), "Binding of vitamin D and cholesterol to beta-lactoglobulin," Journal of Dairy Science 80(6): 1054-1059.
Wang W (2000) "Lyophilization and development of solid protein pharmaceuticals." International Journal of Pharmaceutics 203: 1-60.
Wildman, 1983, "An Alternative Use . . . " In Plants: The Potentials for Extracting Protein . . . , Workshop Proc.; US Congress, Office Tech. Assessment: Wash. D.C., OTA P F 23,pp. 63-77.
Zimet, P. et al. (2009), "Beta-lactoglobulin and its nanocomplexes with pectin as vehicles for ro-3 polyunsaturated fatty acids." Food Hydrocolloids: 23(4): 1120-1126.
PCT International Preliminary Report on Patentability, for parent PCT application PCT/US2011/027399, mailed Sep. 11, 2012 (5 pages).
PCT Written Opinion of the ISR, for parent PCT application PCT/US2011/027399, mailed Dec. 22, 2011 (4 pages).
PCT International Search Report, for parent PCT application PCT/US2011/027399, mailed Dec. 22, 2011 (3 pages).

* cited by examiner

Comparison of vitamin D₃ recovery in freeze-dried formulation: with tobacco leaf protein vs. control Comparison of vitamin D₃ recovery, and crude protein %
in vitamin D-tobacco leaf protein complex of different water content Comparison of vitamin $D_3$ recovery, and crude protein % in vitamin D-tobacco leaf protein complex of varying pH

Figure 4

Solubility values of vitamin D – leaf tobacco protein complex formulated at different pH (p value= 0.0709)

| pH | Solubility |
|---|---|
| 4.3 | 10.78±0.04 |
| 8.5 | 10.27±0.06 |
| 11 | 8.18 ± 2.01 |

Comparison of vitamin $D_3$ recovery and crude protein %
in the vitamin D-tobacco leaf protein complex under different mixing conditions

COMPOSITION OF MATTER FOR DELIVERING LIPID-SOLUBLE MATERIALS, AND A METHOD FOR PRODUCING IT

CROSS REFERENCE TO RELATED APPLICATIONS

This application claims priority from the provisional application Ser. No. 61/311,072 which was filed Mar. 5, 2010, the entire contents of which are incorporated herein by reference.

GOVERNMENT INTERESTS

This invention was made with U.S. government support under USDA-CSREES Awards Nos. 2008-34467-19445 and 2009-34467-20151. The government has certain rights in the invention.

BACKGROUND OF THE INVENTION

For purposes of this invention disclosure, the terms "lipid-soluble" and "lipophilic" refer to compounds or substances which are capable of dissolving in fats, oils, lipids, or non-polar solvents. The terms "lipid-soluble" and "lipophilic" are used interchangeably, and the term "lipophile" refers to a substance which is lipophilic.

Delivery of lipid-soluble materials such as vitamins A, D, E and K, fatty acids and lipid-soluble pharmaceuticals into the human (or animal) body remains a challenge. It can be difficult to maintain lipid-soluble nutrients in low-fat foods because they do not remain in solution and/or they adsorb to packaging materials (Swaisgood et al., 2001). Existing commercial delivery and fortification strategies revolve around emulsification and microencapsulation, both of which have limitations. Emulsification requires product-specific emulsifiers, many of which are not GRAS (Generally Recognized As Safe). Microencapsulation materials, such as cyclodextrins, are often expensive. In addition, these approaches invariably require using a substantial amount of fat as carriers for lipid-soluble materials.

The need for new carriers for lipid-soluble materials has become particularly apparent, given the recent resurgence of vitamin D deficiencies. Vitamin D is associated with bone health, myocardial development, brain and fetal development and reduced cancer risk. While the needs are evident, the means to incorporate vitamin D remain limited, at least in part due to the fact that vitamin D is sensitive to acid, oxygen, and light. Fortification of lipid-soluble vitamins, such as vitamin D, is challenging given their sensitive chemical nature. The presence of conjugated double bonds in vitamin D provides an easy route for decomposition by oxidation. Isomerization can occur under acidic or light conditions. Temperatures above 40° C. and relative humidity above 85% can deteriorate it, while mild acidification can isomerizes it to inactive forms.

Similarly, fortification of foods and beverages with fatty acids, such as polyunsaturated Ω-3 fatty acids, is very challenging because the fatty acids are highly insoluble in water and very sensitive to oxidative degradation which can reduce their health benefits and cause undesirable odors (Zimet et al., 2009).

Protein-based carriers offer a potential alternative to existing carriers, although the limited research to date on protein carriers has focused on dairy proteins. Wang et al. (1997) reported that beta-lactoglobulin, the major protein in whey, showed substantially greater binding affinity to vitamin $D_2$ than to vitamin A. They did not, however, report being able to produce a complex using beta-lactoglobulin and a vitamin. They also did not provide binding efficiency data which would indicate what proportion of the available vitamins the protein was able to bind.

Swaisgood et al. (2001) also used beta-lactoglobulin to form a complex with vitamin D. While they were able to form a complex which was soluble in aqueous solution, their approach involved affinity purification methods, including use of affinity chromatography in their preferred method, which would be cost-prohibitive for commercial applications. The authors also did not provide information about the proportion of the added vitamin D which was retained in the complex along with beta-lactoglobulin.

Zimet et al. (2009) noted that certain food proteins, particularly milk proteins, had an ability to bind to hydrophobic molecules, making them useful for the encapsulation and delivery of bioactive compounds. They reported that beta-lactoglobulin had been found to bind with vitamin D, retinoic acid, cholesterol and various aromatic compounds and fatty acids. They noted, though, that there had been no prior published work on the binding of proteins to Ω-3 fatty acids. Using a complex containing beta-lactoglobulin and pectin, they reported an encapsulation efficiency for DHA (docosahexaenoic acid) of approximately 64% (i.e., amount of DHA encapsulated as a percent of the initially added DHA).

Semo et al. (2007) attempted to use microencapsulation involving pure casein micelles. They wrote that the use of casein micelles as carriers for nutraceuticals had not yet been reported in the literature. However, they were only able to encapsulate approximately 27% of the analytically recovered vitamin $D_2$ which they had added to a suspension containing casein micelles.

The inventors of the present invention have unexpectedly found that using a plant-based protein, leaf protein, they were able to create a leaf protein-vitamin D complex which retained approximately 85% of the vitamin D contained in a mixture—more than three times greater percentages of vitamin D than is reported from casein micelles. The present invention pertains specifically to the use of leaf proteins in a complex with lipid-soluble materials.

The term "leaf protein" as used in this invention disclosure is intended to refer to all water-soluble proteins contained in plant leaves. The leaf protein may be obtained from any green leafy plant, as it is well known that all chlorophyll-containing plants contain soluble leaf proteins. Examples of such plants include, but are not limited to, tobacco, alfalfa and spinach. Lo et al. (2008) and Fu et al. (2010) have described a method for efficiently recovering and preparing a leaf protein powder from the leaves of green plants. Leaf protein may be extracted from plants, and a suitable leaf protein powder prepared, using the method described in Lo et al. (2008), which is incorporated by reference, or using other methods which may be known to practitioners of the art.

Leaf proteins—the proteins which occur naturally in the leaves of green plants—are perhaps the most abundant proteins in nature. They contain excellent binding, gelling, foaming, whipping and emulsifying characteristics, and have nutritional value comparable to milk protein (Lo et al., 2008; Sheen et al., 1991). Leaf protein carriers also offer another advantage over other proteins in that consumers do not have to worry about whether the products contain animal-origin or dairy-based ingredients. Leaf protein is therefore a very desirable carrier for the delivery of lipophilic substances.

SUMMARY OF THE INVENTION

This invention provides a novel composition of matter comprising a complex of leaf protein and one or more lipid-soluble materials. The present invention also provides methods of making and using such complexes.

Complexes of the invention typically comprise leaf protein and one or more lipid-soluble materials such as, for example, vitamins A, D, E, and K, fatty acids, lipid-soluble pharmaceuticals, or other lipid-soluble materials. In a preferred embodiment, the complex is a powdery solid material. This complex is useful as a carrier for the delivery of lipid-soluble materials, into or onto humans or animals. A non-limiting list of examples for the possible uses of this leaf protein—lipid-soluble material complex are as a food or in food as a delivery system for vitamins or other lipid-soluble materials; in dietary supplements and nutraceuticals, infant formulas, in pharmaceuticals or in topical compositions. Nutrient and vitamin supplements can be in any form known in the art, including but not limited to, powders, tablets (chewable or otherwise), capsules, gel-caps, elixirs, and effervescent tablets. Alternatively, nutrient and vitamin supplements can be in the form of bars, drinks, juices or shakes, among others. These and other aspects of the present invention are disclosed in more detail in the description of the invention below.

The inventors were able to produce a leaf protein-vitamin $D_3$ complex which retained approximately 85% of the vitamin D added to a mixture, using a preferred embodiment of the claimed method. (See FIG. 1). This result indicates that leaf protein is highly effective and efficient as a carrier of lipid-soluble materials. Without wishing to be bound by theory, this result also indicates that leaf protein has many binding sites, and is able to carry large amounts of target lipid-soluble materials.

Methods of the invention typically comprise preparing a suspension containing leaf protein. Optionally, non-water-soluble materials may be removed from the leaf protein suspension. Lipid-soluble materials may then be mixed with the suspension. Optionally, lipid-soluble materials may be prepared by dissolving them in a solvent prior to their addition to the suspension. When the leaf protein suspension and the lipid-soluble materials have been suitably combined, they may be further treated. In one embodiment, the mixture may be frozen and, optionally, lyophilized. In some embodiments, the mixture may be dried without freezing using techniques well known in the art, for example, spray drying. In some embodiments, the mixture is dried into a powder. The resulting product is a solid powder containing a complex of leaf protein and the target lipid-soluble material(s).

BRIEF DESCRIPTION OF THE FIGURES

FIG. 4: Solubility values of vitamin D—tobacco leaf protein complex formulated at different pH (p value=0.0709).

DETAILED DESCRIPTION OF INVENTION

Figure 1:
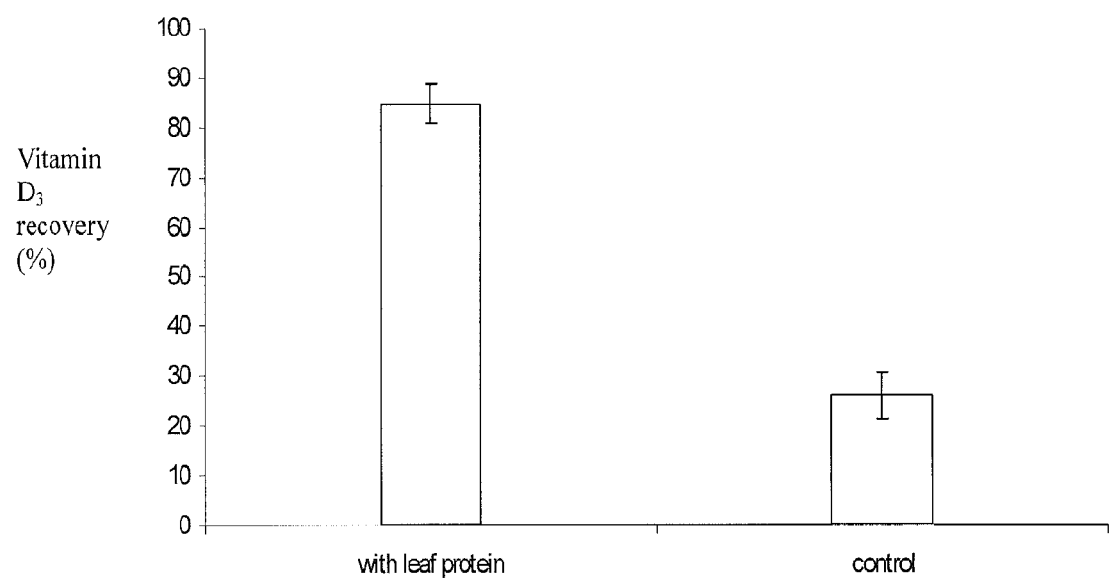
FIG. 1: Comparison of vitamin $D_3$ recovery in freeze-dried formulation: with tobacco leaf protein vs. control.

The principles, preferred embodiments and modes of operation of the present invention will be described hereunder. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the examples, descriptions, and best mode of carrying out the invention given below should be considered exemplary in nature and not as limiting to the scope and spirit of the invention as set forth in the claims.

The objective of the methods of this invention is to produce a complex containing leaf protein and one or more lipid-soluble substances. The present invention may be used to prepare complexes consisting of leaf protein and any other lipid-soluble materials, including but not limited to, vitamins $D_3$, A, E, K, other types of vitamin D, fatty acids such as DHA, eicosapentaenoic acid, linoleic acid, and alpha-linoleic acid, lipid-soluble drugs (some of which are listed below), cholesterol, retinol and retinoids and other lipophilic substances. In some embodiments, complexes of the invention may comprise 2, 3, 4, 5, or more lipid-soluble materials.

The term "target substance" as used in this invention disclosure refers to the particular lipid-soluble substance(s) which the practitioner wishes to form into a complex with leaf protein.

The present invention is based on the discovery that leaf protein very efficiently forms complexes with lipophilic substances, for example vitamin D. This property allows the use of leaf protein as a carrier for lipophilic nutrients in foods, dietary supplements and nutraceuticals, infant formulas, drugs and pharmaceuticals and topical compositions.

Lipid-soluble materials may be derived from any source known in the art, for example, the vitamin A, vitamin D, vitamin E, and vitamin K as used herein can be from any source known in the art. The term "vitamin A" as used herein refers to any form of vitamin A, including but not limited to, retinol, retinaldehydes, retinal, retinoic acid (also known as tretinoin and retin-A), and vitamin A salts and derivatives (e.g., retinol palmitate, retinyl acetate, and β-carotene and other carotenoids). The term "vitamin D" as used herein refers to any form of vitamin D, including but not limited to, ergocalciferol ($D_2$), cholecalciferol ($D_3$), 22,23-dihydroergocalciferol ($D_4$), and vitamin D salts and derivatives (e.g., 25-hydroxycholecalciferol and 1-α,25-dihydroxycholecalciferol). The term "vitamin E" as used herein refers to the family of compounds known as tocopherols (e.g., α-tocopherol, β-tocopherol, δ-tocopherol, γ-tocopherol), as well as tocol, tocoquinone, tocotrienol, and vitamin E salts (e.g., vitamin E phosphate) and derivatives (e.g., tocopherol sorbate, tocopherol acetate, tocopherol succinate, other tocopherol esters). As used herein, the term "vitamin K" refers to vitamin $K_1$ (phytonadione), vitamin $K_2$ (menaquinone), vitamin $K_3$ (menadione), vitamin $K_4$, vitamin $K_5$, vitamin $K_6$, vitamin $K_7$, and their salts and derivatives.

Fatty acids refer to carboxylic acids with a long unbranched aliphatic tail, and which are either saturated or unsaturated. Fatty acids include, but are not limited to DHA, eicosapentaenoic acid, linoleic acid, and alpha-linoleic acid, amongst many others.

Leaf protein powder suitable for practicing this invention may be obtained from plant leaves using the method described in Lo et al. (2008) and Fu et al. (2010), or using any other method of leaf protein processing or extraction which may be known to practitioners in the art.

One suitable method for preparing leaf protein is as follows:

Freshly harvested green plant leaves may be chopped with a hammermill. The leaves can be either freshly harvested, or they can be stored in a cool or frozen state or dried following harvest until they are ready for processing. Alternatively, physical maceration procedures, combined with mechanical pressure, can be utilized to disrupt the cell wall and prepare the proteins for solubilization.

Substantially simultaneously with the leaf rupturing, a buffer solution is added to the leaves. The inventors found that a solution containing sodium phosphate dibasic and potassium phosphate monobasic ($Na_2HPO_4$—$KH_2PO_4$) is especially effective, although other effective buffering agents may be used. The inventors also found that a pH of 7.77 is preferable as it gave the highest protein yields with this agent, although a pH range between approximately 7.4-8.0 or even 6.5-9.0 is acceptable.

It is preferred that the buffer should have a low concentration, in order to avoid precipitating or denaturing the proteins. It was found that a buffer concentration of approximately 0.067M was the optimal concentration, although a range of 0.025M to about 0.3M is quite acceptable, and more preferably a range of about 0.067M-about 0.2 M.

It is preferred that the buffer solution should also contain both a chelating agent and a reducing agent. The purpose of the chelating agent is to remove loose ions from the resulting juice. We have found that 10 mM of EDTA, a well-known chelating agent, is effective to recover loose ions. The purpose of the reducing agent is to prevent oxidation and denaturation of the proteins. We have also found that 25 mM of 2-mercaptoethanol is effective as a reducing agent.

The ruptured leaves may be stored in the buffer solution for up to twenty-four hours, although preferably not more than five hours. While such storage is not necessary, it was found to help improve ultimate protein recovery.

An industrial filter may then be used to filter out the fibrous leaf biomass, leaving a green juice containing the soluble protein. We have found a screw press to give effective results. This green juice contains the soluble proteins along with plant chloroplast materials. Subjecting this green juice to powerful centrifuge will remove this chloroplast material, leaving an "amber juice" which contains the soluble proteins. Centrifuging at a force of approximately 12,000 g for approximately 20 minutes is sufficient to remove leaf chloroplast materials. Either continuous centrifuge or disk centrifuge is suitable. However, failure to adequately centrifuge the green juice will result in incomplete removal of the chloroplasts, and can leave an undesirable green tint in the resulting proteins.

Depending upon the desired use, it is possible to obtain several different protein products from this amber juice.

Product 1—Crude Protein Powder. The simplest approach is to prepare a protein powder product from this resulting amber juice through the use of standard industrial drying processes. This powder product can be prepared using spray drying, vacuum drying or freeze drying. However, spray drying is most practical for scale-up to an industrial level. This crude protein powder could be satisfactory for many commercial uses.

Product 2—Purified Protein Powder. It is possible to remove nucleic acids and small molecule impurities through a precipitation of the amber juice solution at its isoelectric point, which we have found to be at or about pH 5.3 (±0.5). The resulting solution can then be dried via spray drying or other industrial drying techniques to obtain a more highly purified powder product.

Product 3—It is possible to separate ribulose 1.5-bisphosphate carboxylase/oxygenase (RuBisCO) from the amber juice. An isoelectric point precipitation can be conducted at a pH of approximately 5.3 (±0.5), which is the isoelectric point for RuBisCO. This protein can then be centrifuged at a force of approximately 12,000 g or greater. The precipitate is then resuspended in buffer solution at a pH of approximately 7.77. The precipitate is then dried using spray drying or other means to produce a powder product containing RuBisCO. RuBisCO can be further purified if desired.

Product 4—The supernatant from the isoelectric point precipitation at pH 5.3 can be further purified to yield other leaf proteins. A second isoelectric point precipitation can be conducted involving the supernatant at a pH of approximately 4.2 (±0.5). The proteins can then be resuspended in buffer at a pH of approximately 7.77, and then dried using spray drying or other forms of drying.

Any of the above-described leaf protein powders may be used in the practice of the present invention.

The leaf protein powder is then placed in a suitable solvent, such as water, to form a suspension. Failure to place the protein powder into a suitable solvent may inhibit or prevent formation of an effective protein complex, as the dry protein is generally too coarse to efficiently bind or form a complex with a target substance. Additionally, preparing this protein-containing suspension is believed to expose additional binding sites to the target substance. In a preferred embodiment, water is used as the solvent to form the leaf protein aqueous suspension. In a particularly preferred embodiment, the ratio of leaf protein powder to water will be approximately 1 gram of leaf protein powder to between approximately 30 to 80 ml of water. Failure to maintain adequate water content will reduce the capacity of leaf protein to form a complex with the target substance. Use of excessive water content may add drying time and cost, and may reduce interaction of the protein and target substance.

In a preferred embodiment, the pH of the water is adjusted to between 3.3 and 6.3. Using a pH below this range may degrade the leaf protein. Using a pH in the preferred range maintains the structure of the protein, which optimizes its ability to retain the target substance.

In the present invention, the leaf protein forms a complex with one or more target substances in solution. The target substance(s), which is a lipid-soluble material, is solubilized in a suitable organic solvent, such as ethanol, methanol, other alcohols, hexane, acetone, or toluene, amongst many others. One skilled in the art will realize that the optimal organic solvent will depend on the nature of the lipid-soluble material. As an example, ethanol is particularly preferred if vitamin $D_3$ is the target substance.

Following solubilization of the target substance(s), the protein-containing suspension and the target-substance(s)-containing solution are then mixed together and then, in a preferred embodiment, frozen. Several techniques known to practitioners in the art may optionally be used to enhance mixing, for example, magnetic stirring, sonication, vortexing, or a combination of mixing methods. Practitioners in the art will recognize that different mixing techniques may prove more suitable for particular lipid-soluble materials than other techniques. If vitamin $D_3$ is the target substance, a preferred embodiment is the use of magnetic stirring for approximately five minutes.

In a preferred embodiment, freezing should occur within one hour after the protein-containing suspension is mixed with the target-substance-containing solution. In a more preferred embodiment, freezing occurs substantially immediately after the protein-containing suspension is mixed with the target-substance-containing solution. Delays in freezing after mixing the protein-containing suspension with the target-substance-containing solution may reduce the amount of the target substance which forms a complex with the leaf protein. At the time of mixture, the protein and target substance are in close contact. However, they may separate as time is allowed to pass. One skilled in the art will recognize that the rate at which the protein and target substance dissociate will depend on the nature of the target substance(s), and that this will affect the optimal time for freezing to occur.

Any techniques which obtain substantially immediate freezing of the protein-target substance mixture are potentially suitable. A non-limiting list of suitable freezing techniques include use of liquid nitrogen, dry ice or methanol. A preferred embodiment is the use of liquid nitrogen for freezing.

In a preferred embodiment, following freezing, the frozen mixture of protein and the target substance(s) is then dried. Any technique for drying may be suitable, including but not limited to freeze-drying, precipitation, oven-drying, microwaving or a combination of methods. One preferred embodiment is freeze-drying, as this technique will not degrade the protein or target substance. If freeze-drying is used, then the end product will be a powdery material containing a complex which contains leaf protein and the target substance.

The resulting dried complex, containing leaf protein and the lipid-soluble target substance(s), is suitable for use as a food additive, in forming nutrient, vitamin or other dietary supplements or nutraceuticals. Such products can be in any form known in the art, including but not limited to, tablets (including chewable tablets), capsules, gel-caps, powders, elixirs, and effervescent tablets. Alternatively, such products can be in the form of shakes, juices or other drinks, and bars.

The present invention also provides food compositions comprising complexes of leaf protein and lipophilic nutrients. Preferably the lipophilic nutrients are vitamin A, vitamin D, vitamin E, vitamin $K_1$, cholesterol, carotenoids, conjugated linoleic acid, essential fatty acids, and other fatty acids. Because of its excellent nutritional qualities and water-solubility, leaf protein is highly suitable as a suitable carrier for lipophilic nutrients in food compositions. Complexes of leaf proteins and lipophilic nutrients are also useful for fortifying infant formulas with DHA and other lipid-soluble substances.

The food compositions of the present invention are formed by combining a leaf protein—lipid-soluble material complex according to the present invention with other food ingredients. Alternately stated, a food composition is a food product containing a leaf protein—lipid-soluble material complex of the present invention as an ingredient or component. A food composition can be a liquid or a solid food for human or animal consumption, and includes, but is not limited to, dairy products, processed meats, breads, cakes and other bakery products, processed fruits and vegetables, etc.

The present invention also includes compositions comprising a leaf protein—lipid soluble material complex, in which the leaf protein forms a complex with a lipophilic drug for delivery into humans or animals. Such compositions can be in any form known in the art, including but not limited to, tablets (including chewable tablets), capsules, gel-caps, powders, elixirs, and effervescent tablets. A non-limiting list of lipophilic drug substances which may used to form a leaf-protein—lipid-soluble material complex according to the present invention includes the following: Analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole; Anti-arrhythmic agents: amiodarone, disopyramide, flecamide acetate, quinidine sulphate; Anti-bacterial agents: benethamine penicillin, cinoxacin, ciprofloxacin, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; Anti-coagulants: dicoumarol, dipyridamole, nicoumalone, phenindione; Anti-depressants: amoxapine, maprotiline, mianserin, nortriptyline, trazodone, trimipramine maleate; Anti-diabetics: acetohexamide, chlorpropamide, glibenclamide, gliclazide, glipizide, tolazamide, tolbutamide; Anti-epileptics: beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid; Anti-fungal agents: amphotericin, butoconazole nitrate, clotrimazole, econazole nitrate, fluconazole, flucyto sine, griseofulvin, itraconazole, ketoconazole, miconazole, natamycin, nystatin, sulconazole nitrate, terbinafine, terconazole, tioconazole, undecenoic acid; Anti-gout agents: allopurinol, probenecid, sulphin-pyrazone;] Anti-hypertensive agents: amlodipine, benidipine, darodipine, dilitazem, diazoxide, felodipine, guanabenz acetate, isradipine, minoxidil, nicardipine, nifedipine, nimodipine, phenoxybenzamine, prazosin, reserpine, terazosin; Anti-malarials: amodiaquine, chloroquine, chlorproguanil, halofantrine, mefloquine, proguanil, pyrimethamine, quinine sulphate; Anti-migraine agents: dihydroergotamine mesylate, ergotamine tartrate, methysergide maleate, pizotifen maleate, sumatriptan succinate; Anti-muscarinic agents: atropine, benzhexyl, biperiden, ethopropazine, hyoscyamine, mepenzolate bromide, oxyphencylcimine, tropicamide; Anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine, tamoxifen citrate, testolactone. tacrolimus, sirolimus; Anti-protozoal agents: benznidazole, clioquinol, decoquinate, diiodohydroxyquinoline, diloxanide furoate, dinitolmide, furzolidone, metronidazole, nimorazole, nitrofurazone, omidazole, timidazole; Anti-thyroid agents: carbimazole, propylthiouracil; Alixiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, baloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone; beta-Blockers: acebutolol, aiprenolol, atenolol, labetalol, metoprolol, nadolol, oxprenolol, pindolol, propranolol; Cardiac Inotropic agents: amrinone, digitoxin, digoxin, enoximone, lanatoside C, medigoxin; Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; Diuretics: acetazolamide, amiloride, bendrofluazide, bumetanide, chlorothiazide, chlorthalidone, ethacrynic acid, frusemide, metolazone, spironolactone, triamterene; Antiparkinsonian agents: bromocriptine mesylate, lysuride maleate; Gastro-intestinal agents: bisacodyl, cimetidine, cisapride, diphenoxylate, domperidone, famotidine, loperamide, mesalazine, nizatidine, omeprazole, ondansetron, ranitidine, sulphasalazine; Histamine H-Receptor Antagonists: acrivastine, astemizole, cinnarizine, cyclizine, cyproheptadine, dimenhydrinate, flunarizine, loratadine, meclozine, oxatomide, terfenadine; Lipid regulating agents: bezafibrate, clofibrate, fenofibrate, gemfibrozil, probucol; Nitrates and other anti-anginal agents: amyl nitrate, glyceryl trinitrate, isosorbide dinitrate, isosorbide mononitrate, pentaerythritol tetranitrate; HIV protease inhibitors: Nelfinavir; Opioid analgesics: codeine, dextropropyoxyphene, diamorphine, dihydrocodeine, meptazinol, methadone, morphine, nalbuphine, pentazocine; Sex hormones: clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone; Stimulants: amphetamine, dexamphetamine, dexfenfluramine, fenfluramine, and mazindol. (See Benita et al., 2007 regarding a list of lipophilic drugs).

The present invention also includes compositions for use in personal care and/or hygiene comprising the leaf protein—lipid-soluble material complexes disclosed herein (e.g., soaps, skin creams, soaps, cleansers, shampoos). Topical compositions containing complexes of leaf protein with vitamin E, vitamin A, conjugated linoleic acid, and essential fatty acids are preferred. The topical compositions disclosed herein are suitable for topical application to mammalian skin. The compositions comprise a safe and effective amount of the leaf protein complexes and other active agents, and a cosmetically- and/or pharmaceutically-acceptable topical carrier.

The phrase "cosmetically- and/or pharmaceutically-acceptable carrier", as used herein, means any substantially non-toxic carrier suitable for topical administration to the skin, which generally has good aesthetic properties, and is compatible with the leaf protein—lipid-soluble material complexes of the present invention. By "compatible" it is meant that the leaf protein—lipid-soluble material complexes will remain stable and retain substantial activity therein. The carrier can be in a wide variety of forms, such as sprays, emulsions, mousses, liquids, creams, oils, lotions, ointments, gels and solids. Suitable pharmaceutically-acceptable topical carriers include, but are not limited to, water, glycerol, alcohol, propylene glycol, fatty alcohols, triglycerides, fatty acid esters, and mineral oils. Suitable topical cosmetically-acceptable carriers include, but are not limited to, water, petroleum jelly, petrolatum, mineral oil, vegetable oil, animal oil, organic and inorganic waxes, such as microcrystalline, paraffin and ozocerite wax, natural polymers, such as xanthanes, gelatin, cellulose, collagen, starch or gum arabic, synthetic polymers, alcohols, polyols, and the like. Preferably, because of its non-toxic topical properties, the pharmaceutically- and/or cosmetically-acceptable carrier is substantially miscible in water. Such water miscible carrier compositions can also include sustained or delayed release carriers, such as liposomes, microsponges, microspheres or microcapsules, aqueous based ointments, water-in-oil or oil-in-water emulsions, gels and the like.

The disclosed complex is also suitable as a component of tissue culture media or microbial growth media to promote growth, differentiation and/or viability of cultured cells. Milk proteins have been shown to be a suitable fatty acid carrier in cell culture (Swaisgood et al., 2001), and therefore leaf proteins should be similarly suitable.

EXAMPLES

Example 1

Evaluation of Different Strategies for Solubilizing Leaf Protein

The purpose of this test was to evaluate different strategies for solubilizing the leaf protein. It is necessary to solubilize the leaf protein in order to remove residual pigments, fat content and other form a complex with the target lipid-soluble molecules.

Protein samples were subjected to solvent extraction with three organic solvents; hexane; acetone and methanol. Leaf protein powder prepared by the method of Lo et al. (2008) and Fu et al. (2010) has a water solubility value of 10.08±0.15 grams/liter (g/l). Hexane extraction of the protein powder yielded only a marginal increase in solubility of 10.82 g/l, whereas acetone extraction showed even smaller increase in solubility and methanol actually caused solubility to decrease. Based on these findings, the inventors did not utilize a solvent as pretreatment prior to mixing with vitamin D.

Example 2

Effect of Water Content on Leaf Protein Lipophile Complex

Leaf protein samples were derived from Maryland tobacco variety 609LA, a low-alkaloid variety containing 0.6 mg/g to 0.8 mg/g of nicotine, using the method described in Lo, et al. (2008) and Fu et al. (2010). One gram of leaf protein powder was placed in a 300-ml freeze-drying glass flask (F05657000, Thermoscientific, Pittsburgh, Pa.), followed by addition of either 20 ml or 40 ml of water and 4 ml of vitamin $D_3$ in 99% pure ethanol (1000 ug/ml). The pH of the mixture was adjusted to pH 4.3 by gradually adding 1 M sodium hydroxide solution to the protein water solution prior to adding vitamin $D_3$. This mixture was then magnetically stirred for 4 minutes before liquid nitrogen was added. Approximately 250 ml of liquid nitrogen was poured into the glass until the mixture appeared completely solid. The flask was then immediately closed with the lid and carefully placed in a thermally insulated bag filled with dry ice. The connector end of the freeze-drying flask was connected to the freeze-dryer (RVT4104 model Refrigerated Vapor Trap, Thermo Electron Corporation, NY) at −110° for 96 hours.

Figure 2:
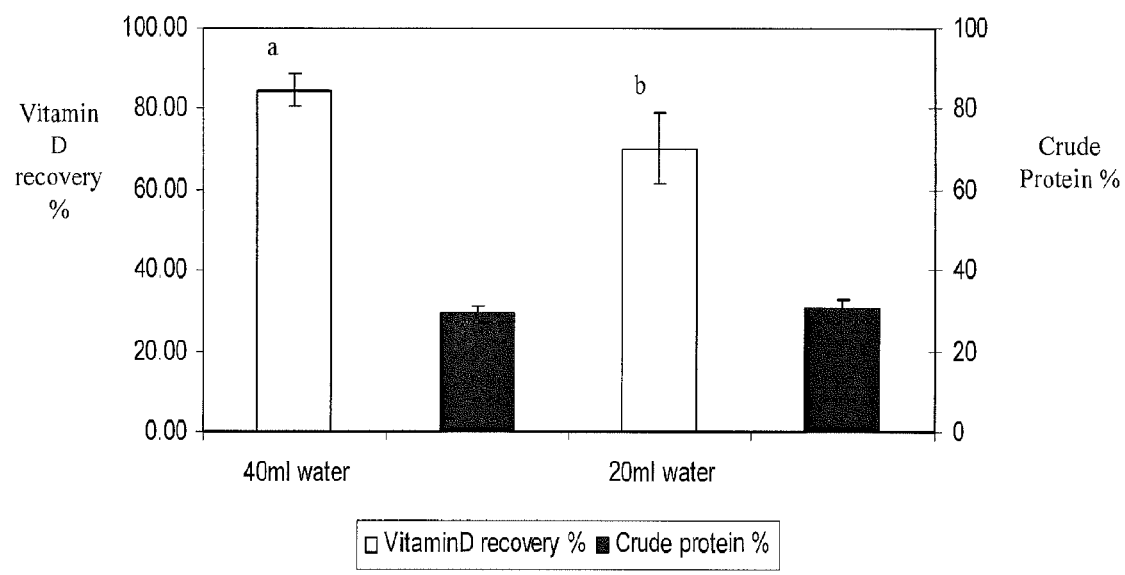
FIG. 2: Comparison of vitamin $D_3$ recovery, and crude protein % in vitamin D-tobacco leaf protein complex of different water content.

Using 40 ml of water per gram of leaf protein powder to obtain the vitamin D-protein complex, the inventors obtained a vitamin $D_3$ recovery of 84.68±3.92% of the total vitamin $D_3$ added. In contrast, use of only 20 ml of water per gram of protein powder significantly reduced the vitamin $D_3$ recovery to 70.21±8.92%. (See FIG. 2). The inventors observed that the spherical structure in the protein aggregates could not be maintained at the lower water content levels. Without wishing to be bound by theory, the inventors hypothesize that the increased water level at 40 ml helped form hydrogen bonds which maintained the protein structure. Conversely, at the lower water content level (which corresponded with higher protein density), self-stabilization of proteins may have taken place where proteins tended to form bonds which interconnected adjacent proteins, reducing the sites available for vitamin $D_3$ binding as well as limited surface area of ice-/water interface during the freeze-drying process.

Example 3

Effect of pH on Leaf Protein

Lipophile Complex

The inventors measured the effect of pH on the leaf protein—lipophile complex. They used the same preparation as described above in Example 2, except that they only used one water content level: one gram of leaf protein per 40 ml of water. They also prepared the leaf protein-vitamin D mixture described in Example 2 at three different pH levels (4.3, 8.5 and 11.0). As noted above, for pH adjustment, 1 M sodium hydroxide solution was gradually added to the protein water solution prior to adding vitamin $D_3$.

Figure 3:
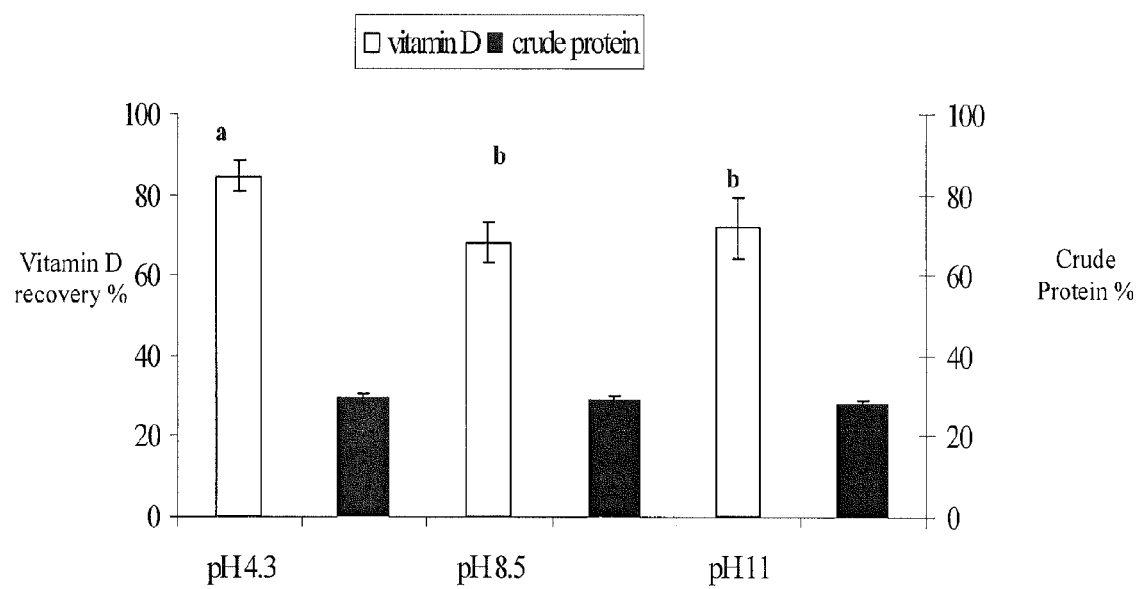
FIG. 3: Comparison of vitamin $D_3$ recovery, and crude protein % in vitamin D-tobacco leaf protein complex of varying pH.

The sample tested at pH 4.3 showed substantially higher recovery of vitamin $D_3$ (84.6%±3.92%, w/w) than either of the two other treatments. (See FIG. 3). There was also a slight increase in the water solubility of the vitamin D-protein complex at pH 4.3 from 10.08 to 10.78 g/l (See FIG. 4).

In each of the three treatments, the crude protein represented about 30% of the vitamin $D_3$-tobacco leaf protein complex.

It is generally recognized that changes in pH can induce significant alterations in protein structure. At pH 4.3, the vitamin $D_3$-protein complex appeared to be spherical aggregates. As the pH increased to 8.5, the spherical structure opened up and bridged with adjacent aggregates, forming an interwoven structure. At pH 11.0, the spherical structure was completely disrupted, forming a continuous porous structure. In other words, porosity increased as the pH increased, corresponding to the loss of vitamin D. Without wishing to be bound by theory, the inventors believe that this increase in porosity was related to a loss of vitamin D. Again without wishing to be bound by theory, the inventors believe that that the lower porosity and spherical aggregate structure of the protein at the lower pH permitted the protein to retain or "trap" the vitamin D so it could not escape.

Example 4

Effect of Protein-Vitamin Mixing Technique on Vitamin Carrying Capacity

This test measured the effect of different techniques for mixing protein and vitamin $D_3$ on the protein's vitamin $D_3$ carrying capacity. They used the same preparation as described above in Example 2, except that they only used one water content level: one gram of leaf protein per 40 ml of water. The inventors also tested three mixing treatments: (i) magnetic stirring for 5 minutes, (ii) a Sonicator (28H ultrasonic bath, Neytech, Bloomfield, Conn.) at a frequency of 47±3 khZ for 5 minutes; and (iii) a combination involving the sonication treatment followed by the stirring treatment.

Figure 5:
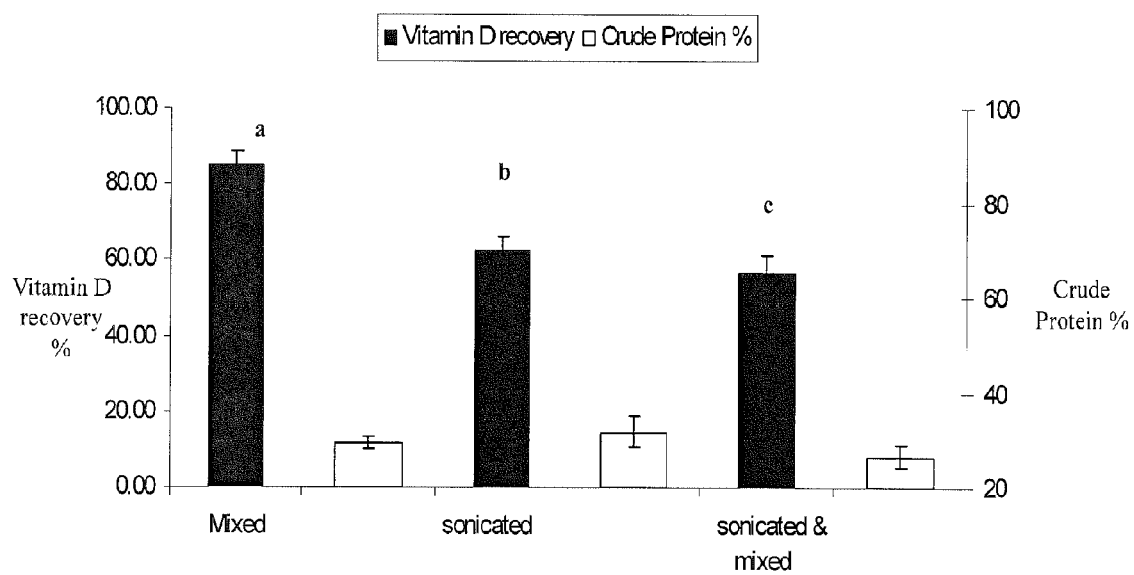
FIG. 5: Comparison of vitamin $D_3$ recovery and crude protein % in the vitamin D-tobacco leaf protein complex under different mixing conditions.

The highest vitamin recovery was obtained when the samples were stir-mixed for 5 minutes, reaching 84.68%±3.92%, w/w (weight/weight). Sonication alone resulted in a substantial reduction in vitamin $D_3$ recovery 62.53%±3.68%, w/w. The temperature increased by 20° C. following sonication. Without wishing to be bound by theory, the inventors hypothesize that the sharp change in temperature may have caused degradation of vitamin $D_3$. Vitamin $D_3$ recovery was lowest when the samples were treated by both sonication and mixing (56.32±5.11%, w/w), likely due to the exposure of vitamin $D_3$ under elevated temperature for an extension of 5 minutes during the mixing process. (See FIG. 5). The crude protein content remained statistically the same in all three differentially mixed formulations.

REFERENCES

Abismaïl, B, J. Canseiler, A. Wilhelm, H. Delmas and C. Gourdon (1999), "Emulsification by ultrasound: drop size distribution and stability." *Ultrasonics Sonochemistry* 6: 75-83.

Allison S., A. Dong A, J. Carpenter (1996), "Counteracting effects of thiocyanate and sucrose on chymotrypsinogen secondary structure and aggregation during freezing, drying and rehydration." *Biophysical Journal*. 71: 2022-2032.

Banville, C, J. Villemard, C. Lacroix (2000), "Comparison of different methods for fortifying Cheddar cheese with Vitamin D." *International Dairy Journal* 10: 375-382.

Carrasquilo K G, Sanchez C, Griebenow K (2000), "Relationship between conformational stability and lyophilisation induced structural changes in chymotrypsin." *Biotechnology and Applied Biochemistry* 31, 41-53.

Forrest, S., R. Yada, D. Rousseau (2005), "Interactions of vitamin $D_3$ with bovine β-lactoglobulin A and β-casein." *Journal of Agricultural and Food Chemistry* 53: 8003-8009.

Fu, H., P. Machado, T. Hahm, R. Kratochvil, C. Wei and Y. Lo (2010), "Recovery of nicotine-free proteins from tobacco leaves using phosphate buffer system under controlled conditions." *Bioresource Technol:* 101 (6): 2034-2042.

Hudson, B and I. Karis (1973), "Aspects of vegetable structural lipids. I. The lipids of leaf protein concentrate." *Journal of the Science of Food and Agriculture* 24: 1541-1550.

Hsu, C. H. Nguyen, D. Yeung, D. Brooks, G. Koe, T. Bewley, R. Pearlman (1995), "Surface denaturation at solid-void interface—a possible pathway by which opalescent particulates form during the storage of lyophilized tissue-type plasminogen activator at high temperatures." *Pharm. Res.* 12: 69-77.

Mozafari, M, C. Johnson, S. Hatziantoniou, C. Demetzos (2008), "Nanoliposomes and their applications in food nanotechnology." *Journal of Liposome Research* 18: 309-327.

Qi, M., N. Hettiarachchy, U. Kalapathy (1997), "Solubility and emulsifying properties of soy protein isolates modified by pancreatin." *J. Food Sci.* 62(6): 1110-1115.

Semo E, Kesselman E, Danino D, Livney D (2007), "Casein micelles as a natural nano-capsular vehicle for nutraceuticals." *Food hydrocolloids,* 21, 936-942.

Sharma A, U. Sharma (1997), "Liposomes in drug delivery: progress and limitations." *International Journal of Pharmaceutics* 154: 123-140.

Sheen J., (1991), "Comparison of chemical and functional properties of soluble leaf proteins from four plant species." *Journal of Agricultural and Food Chemistry,* 39, 681-685.

Sheen, J. V. Sheen (1985), "Functional properties of Fraction 1 Protein from tobacco leaf." *Journal of Agricultural and Food Chemistry* 33: 79-83.

Tso, T. C. (2006), "Tobacco research and its relevance to science, medicine and industry." *Contributions to Tobacco Research* 22: 133-146.

Tso, T. C. (1990). Production, Physiology, and Biochemistry of Tobacco Plant, Ch. 22: Organic Metabolism—Tobacco Proteins." Ideals, Inc., Beltsville, Md.

Tso, T. S. Kung (1983), "Soluble proteins in tobacco and their potential use." In: Leaf Protein Concentrates, Tehel L and Graham D G (eds.), Avi Publishing Company Inc., Connecticut, pp. 117-131.

Wang, Q., J. Allen and H. Swaisgood (1997), "Binding of vitamin D and cholesterol to beta-lactoglobulin," *Journal of Dairy Science* 80(6): 1054-1059.

Wang W (2000) "Lyophilization and development of solid protein pharmaceuticals." *International Journal of Pharmaceutics* 203: 1-60.

Wildman S G (1983), "An Alternative Use for Tobacco Agriculture: Protein for Food Plus a Safer Smoking Material." In Plants: The Potentials for Extracting Protein, Medicines, and Other Useful Chemicals—Workshop Proceedings; US. Congress, Office of Technology Assessment: Washington, D.C., OTA-BP-F-23, pp 63-77.

Zimet, P. et al. (2009), "Beta-lactoglobulin and its nanocomplexes with pectin as vehicles for ω-3 polyunsaturated fatty acids." *Food Hydrocolloids:* 23(4): 1120-1126.

U.S. Pat. No. 6,290,974 to Swaisgood, et al.
U.S. Pat. No. 5,597,595 to DeWille, et al.
U.S. Pat. No. 5,462,593 to Poppe, et al.
U.S. Pat. No. 4,737,367 to Langer, et al.
U.S. Pat. No. 4,554,333 to Krinski, et al.
U.S. Pat. No. 4,144,895 to Fiore, et al.
WO/2010/045648 to Lo, et al.
WO/2008/143914 to Lo, et al.
WO/2007/083316 to Benita, et al.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

Modifications may be made without departing from the basic spirit of the present invention. Accordingly, it will be appreciated by those skilled in the art that within the scope of the appended claims, the invention may be practiced other than has been specifically described herein.

What is claimed is:

1. A freeze-dried or spray-dried powder composition comprising one or more of the vitamins A, D, D2, D3, E or K, bound to a carrier consisting of leaf protein extracted from tobacco, alfalfa or spinach leaves.

2. The freeze-dried or spray-dried powder composition according to claim 1 wherein the composition is a food or food ingredient intended for human consumption.

3. A dietary supplement, nutritional supplement, or nutraceutical comprising the composition of claim 1.

4. A product intended for consumption by mammals other than humans comprising the composition of claim 1.

5. A topical composition comprising the freeze-dried or spray-dried composition of claim 1, and a pharmaceutically acceptable topical carrier.

6. The freeze-dried or spray-dried powder composition according to claim 1 wherein the leaf protein constitutes at least 20% of the composition.

7. The freeze-dried or spray-dried powder composition of claim 1, wherein said composition is produced by (a) providing a suspension comprising extracted leaf protein in a solvent; (b) combining the leaf protein suspension with one or more of vitamins A, D, D2, D3, E or K (c) allowing the leaf protein to bind with the one or more of vitamins A, D, D2, D3, E or K, and (d) forming the composition into a powder, tablet, capsule, gel-cap, elixir or effervescent tablet.

8. The freeze-dried or spray-dried powder of claim 1, wherein the leaf protein is crude leaf protein and comprises about 30% of the composition.

* * * * *